United States Patent [19]

Otsu et al.

[11] Patent Number: 5,596,017
[45] Date of Patent: Jan. 21, 1997

[54] SULFAMIDE DERIVATIVES

[75] Inventors: Yuichi Otsu; Yoshinori Kitagawa, both of Tochigi; Yumi Hattori, Ibaraki; Katsuaki Wada, Tochigi; Toru Obinata, Tochigi, all of Japan

[73] Assignee: Nihon Bayer Agrochem K.K., Tokyo, Japan

[21] Appl. No.: 445,156

[22] Filed: May 19, 1995

[30]  Foreign Application Priority Data

May 27, 1994 [JP] Japan .................................. 6-136599
Mar. 13, 1995 [JP] Japan .................................. 7-079301

[51] Int. Cl.$^6$ ....................... A01N 41/04; C07C 309/65; C07C 309/66
[52] U.S. Cl. .................. 514/517; 558/58; 558/54; 558/53
[58] Field of Search ................... 558/53, 54, 58; 514/517

[56]  References Cited

U.S. PATENT DOCUMENTS

| | | |
|---|---|---|
| 4,331,680 | 5/1982 | Giles et al. . |
| 4,344,893 | 8/1982 | Copping et al. . |
| 4,394,387 | 7/1983 | Copping et al. . |
| 4,432,994 | 2/1994 | Giles et al. . |
| 4,980,373 | 12/1990 | Kisida et al. . |

FOREIGN PATENT DOCUMENTS

| | | |
|---|---|---|
| 0003913 | 9/1979 | European Pat. Off. . |
| 0026040 | 4/1981 | European Pat. Off. . |
| 0353641 | 2/1990 | European Pat. Off. . |

OTHER PUBLICATIONS

Derwent Abstract of JP 04–01 173, (Jan. 1992).
Chemical Abstracts, vol. 51, abstract No. 4372g, (1957).
Derwent Abstracts AN=91–136915/19 (1989).
Derwent Abstracts AN=92–053936/07 (1990).

*Primary Examiner*—Nicky Chan
*Attorney, Agent, or Firm*—Sprung Horn Kramer & Woods

[57]  ABSTRACT

Novel pesticidal sulfamide derivatives of the formula

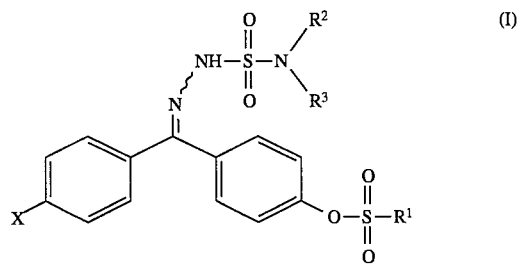

in which
X is halogen or $C_1$–$C_4$-halogenoalkyl,
$R^1$ is $C_1$–$C_4$-alkyl or $C_1$–$C_4$-halogenoalkyl,
$R^2$ is hydrogen or $C_1$–$C_4$-alkyl, and
$R^3$ is hydrogen, $C_1$–$C_4$-alkyl, $C_1$–$C_4$-alkoxycarbonyl or $C_1$–$C_4$-alkoxycarbonylmethyl.

12 Claims, No Drawings

SULFAMIDE DERIVATIVES

The present invention relates to sulfamide derivatives, to a process for their preparation, and their use as pesticides.

It has already been disclosed that certain hydrazone derivatives have insecticidal properties (see Japanese Patent Laid-Open Application Nos. Sho 54-122261, Sho 56-45459 Hei 9-138246, Hei 3-74356 and Hei 4-1173).

However, the activity of these previously known compounds is not entirely satisfactory in all fields of application, in particular at low application rates and concentrations.

There have been found novel sulfamide derivatives of the formula (I)

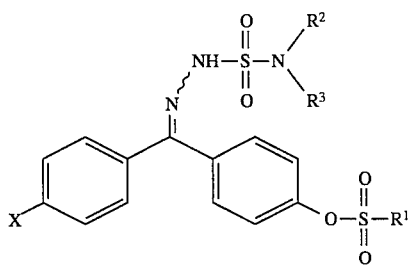

in which
X represents halogen or $C_1$-$C_4$-halogenoalkyl,
$R^1$ represents $C_1$-$C_4$-alkyl or $C_1$-$C_4$-halogenoalkyl,
$R^2$ represents hydrogen or $C_1$-$C_4$-alkyl, and
$R^3$ represents hydrogen, $C_1$-$C_4$-alkoxycarbonyl or $C_1$-$C_4$-alkoxycarbonylmethyl.

It is, for example, well known, that hydrazones exist in two isomeric forms, i.e. syn and anti. This is indicated by the zigzag line between the doubly bonded nitrogen atom and the adjacent nitrogen atom.

Depending also on the nature of the substituents, the compounds of the formula (I) can exist as geometric and/or optical isomers or variously composed isomer mixtures. The invention relates to the pure isomers and also to the isomer mixtures and/or all forms.

Furthermore, it has been found that the compounds of the formula (I) are obtained, when compounds of the formula (II)

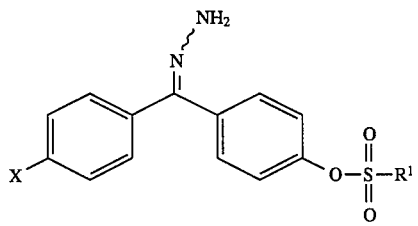

wherein
X and $R^1$ have the abovementioned meanings, are reacted with compounds of the formula (III)

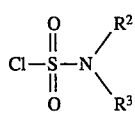

wherein
$R^2$ and $R^3$ have the abovementioned meanings, if appropriate in the presence of a base and, if appropriate in the presence of an inert diluent.

Furthermore, it has been found that compounds of the formula (I) are highly suitable for combating animal pests. In particular, they are distinguished by a powerful activity against arthropods.

Unexpectedly and surprisingly, compounds of the formula (I) according to the invention exhibit substantially better activity against animal pests than the previously known compounds which are described in, for example, the abovementioned Japanese Patent Laid-Open Application (Kokai) Sho 54-122261, Japanese Patent Laid-Open Application (Kokai) Sho 56-45452, Japanese Patent Laid-Open Application (Kokai) Hei 2-138246, Japanese Patent Laid-Open Application (Kokai) Hei 3-74356 and Japanese Patent Laid-Open Application (Kokai) Hei 4-1173, which are most similar with regard to constitution.

Preferred are compounds of the formula (I), in which
X represents fluoro, chloro, bromo or $C_1$-$C_2$-halogenoalkyl,
$R^1$ represents $C_1$-$C_2$-alkyl or $C_1$-$C_2$-halogenoalkyl,
$R^2$ represents hydrogen or $C_1$-$C_2$-alkyl and
$R^3$ represents hydrogen, $C_1$-$C_4$-alkyl, $C_1$-$C_4$-alkoxycarbonyl or $C_1$-$C_2$-alkoxycarbonylmethyl.

Particularly preferred are compounds of the formula (I), in which
X represents fluoro, chloro or trifluoromethyl,
$R^1$ represents methyl or trifluoromethyl,
$R^2$ represents hydrogen, methyl or ethyl and
$R^3$ represents hydrogen, methyl, ethyl, n-propyl, i-propyl, n-butyl, methoxycarbonyl, ethoxycarbonyl, tert.-butoxycarbonyl or methoxycarbonylmethyl.

Very particularly preferred are compounds of the formula (I), in which
X represents fluoro or chloro,
$R^1$ represents methyl,
$R^2$ represents hydrogen and
$R^3$ represents ethyl, n-propyl; isopropyl, butyl or methoxycarbonylmethyl.

As specific examples of compounds of the formula (I) according to the invention, mention can be made of compounds listed in Table 1 given below.

TABLE 1

| X | $R^1$ | $R^2$ | $R^3$ |
|---|---|---|---|
| F | $CH_3$ | H | $CH_3$ |
| F | $CH_3$ | H | $CH_2CH_3$ |
| Cl | $CH_3$ | H | H |
| Cl | $CH_3$ | H | $CH_3$ |
| Cl | $CH_3$ | H | $CH_2CH_3$ |
| Cl | $CH_3$ | H | $CH_2CH_2CH_3$ |
| Cl | $CH_3$ | H | $CH(CH_3)_2$ |
| Cl | $CH_3$ | H | $CH_2CH_2CH_2CH_3$ |
| Cl | $CH_3$ | H | $CH_2-CO_2CH_3$ |
| Cl | $CH_3$ | H | $CO_2-CH_2CH_3$ |
| Cl | $CH_3$ | H | $CO_2-C(CH_3)_3$ |
| F | $CH_3$ | H | $CH(CH_3)_2$ |
| Cl | $CF_3$ | H | $CH_3$ |
| $CF_3$ | $CH_3$ | H | $CH_3$ |
| Cl | $CH_3$ | $CH_3$ | $CH_3$ |
| Cl | $CF_3$ | H | $CH(CH_3)_2$ |
| $CF_3$ | $CH_3$ | H | $CH_2CH_3$ |
| Cl | $CH_3$ | $CH_3$ | $CH_2CH_2CH_3$ |
| F | $CH_3$ | $CH_3$ | $CH_3$ |
| Cl | $CH_3$ | $CH_3$ | $CH_3$ |

TABLE 1-continued

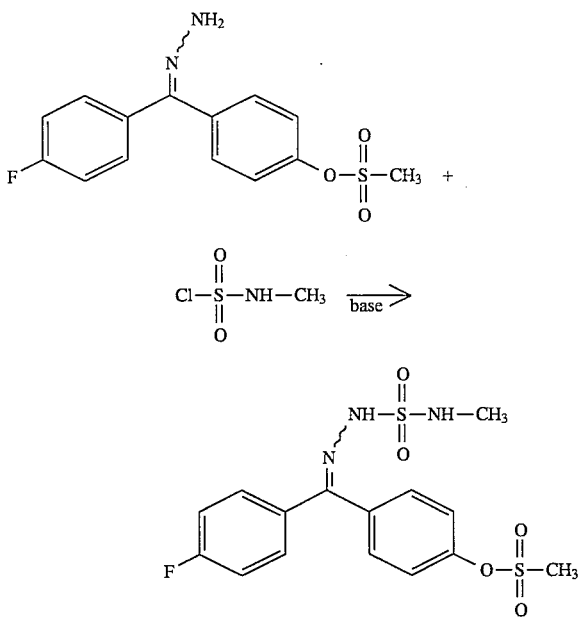

| X | R¹ | R² | R³ |
|---|----|----|----|
| F | CH₃ | H | CH₃ |
| F | CH₃ | CH₂CH₃ | CH₂CH₃ |
| Cl | CH₃ | CH₂CH₃ | CH₂CH₃ |
| Cl | CF₃ | H | CH₂CH₃ |

If, for example, 4-fluoro-4'-methanesulfonyloxybenzophenone hydrazone and N-methylsulfamoyl chloride are used as starting materials, the course of the reaction can be represented by the following equation:

Formula (II) provides a general definition of the hydrazones to be used as starting substances in the process according to the invention for the preparation of the compounds of the formula (I). In formula (II), X and $R^1$ preferably, or in particular, have that meaning which has already been mentioned above in connection with the description of the compounds of the formula (I) as being preferred, or particularly preferred, for X and $R^1$.

The compounds of the formula (II) are known and described in Japanese Patent Laid-Open Application No. Sho 56-45452 and so on. As examples there may be mentioned:
4-fluoro-4'-methanesulfonyloxybenzophenone hydrazone,
4-chloro-4'-methanesulfonylbenzophenone hydrazone,
4-fluoro-4'-trifluoromethanesulfonyloxybenzophenone hydrazone and
4-chloro-4'-trifluoromethanesulfonyloxybenzophenone hydrazone.

Formula (III) provides a general definition of the sulfamoyl chlorides furthermore to be used as starting substances in the process according to the invention for the preparation of the compounds of the formula (I). In formula (III), $R^2$ and $R^3$ preferably, or in particular, have those meanings which have already been mentioned above in connection with the description of the compounds of the formula (I) as being preferred, or particularly preferred, for $R^2$ and $R^3$.

The compounds of the formula (III) are known and described, for example, in Houben-Weyl, Methoden der organischen Chemie, Band XI/2, page 693, 1958, and ibid., Band E XI, page 994, 1985, published by Georg Thieme Verlag. As examples there may be mentioned:
N-methylsulfamoyl chloride,
N,N-dimethylsulfamoyl chloride,
N-ethylsulfamoyl chloride,
N-propylsulfamoyl chloride,
N-isopropylsulfamoyl chloride,
N-butylsulfamoyl chloride and
N-methoxycarbonylmethylsulfamoyl chloride.

In carrying out the above-mentioned preparation process (a), any suitable inert organic solvent can be used as a diluent.

As examples of such diluents, mention can be made of aliphatic, cycloaliphatic and aromatic hydrocarbons which are optionally chlorinated, for example, pentane, hexane, cyclohexane, petroleum ether, ligroin, benzene, toluene, xylene, dichloromethane, chloroform, carbon tetrachloride, 1,2-dichloroethane, chlorobenzene, dichlorobenzene, etc.; ethers, such as ethyl ether, methyl ethyl ether, isopropyl ether, butyl ether, dioxane, dimethoxyethane (DME), tetrahydrofuran (TFIF), diethylene glycol dimethylether (DGM), etc.; ketones, such as acetone, methyl ethyl ketone (MEK), methyl isopropyl ketone, methyl isobutyl ketone (MIBK), etc.; nitriles, such as acetonitrile, propionitrile, acrylonitrile, etc.; esters, such as ethyl acetate, amyl acetate, etc.; acid amides, such as dimethyl formamide (DMF), dimethyl acetamide (DNIA), N-methylpyrrolidone, 1,3-dimethyl-2-imidazolidinone, hexamethylphosphoric triamide (HMPA), etc.; sulfones and sulfoxides, such as dimethyl sulfoxide (DMSO), sulfolane, etc.

The process according to the invention can be carried out in the presence of a base, and as examples of such bases, mention can be made of inorganic bases, for example alkali metal hydroxides, carbonates and bicarbonates, such as sodium hydrogencarbonate, potassium hydrogencarbonate, sodium carbonate, potassium carbonate, lithium hydroxide, sodium hydroxide, potassium hydroxide or calcium hydroxide.

As organic bases, mention can be made of alcoholates, tertiary amines, dialkylanilines and pyridines, such as sodium methylate, potassium tert-butylate, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2.2.2]octane (DABCO) and 1,8-diazabicyclo[5.4.0]undec-7-ene (DBU), and the like.

When carrying out the process according to the invention, the reaction temperatures can be varied within a substantial range. In general, the process is carried out at temperatures between about 0° C. and about 120° C., preferably at temperatures between about 20° C. and about 80° C. The reaction is effected preferably under normal pressure, but the operation can also be carried out under elevated pressure or reduced pressure.

In carrying out the preparation process (a), a compound of the formula (II) is reacted with a compound of the formula (III), for example, in proportions of 1 mole of the compound of the formula (II) and 1–1.2 moles of the compound of the formula (III) in a diluent, for example, dichloroethane, in the presence of triethylamine, whereby a desired compound can be obtained.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field.

They are active against normally sensitive and resistant species and against all or individual development stages. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec..

From the order of the Symphyla, for example, *Scutigerella immaculate.*

From the order of the Thysanura, for example, *Lepisrna saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

Front the order of the Anoplura, for example, *Phylloxera vastatrix,* Pemphigus spp., *Pediculus humanus corpotis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

Front the order of the Heteroptera, for example, Eurygaster spp., *Dysdercus intermedius, Piestoa quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Photodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia amibuguella, Homona magnanima* and *Tortris viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Altagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Dipdon spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus sp., Hypoderma spp., Tabanus spp., Tannin spp., *Bibio hortulanus, Oscinella frit,* Phorbia spp., *Pegomyia hyoscyami, Ceratitis capitata, Dacus oleae* and *Tipula paludosa.*

The active compounds can be converted into the customary formulations, such as solutions, emulsions, wettable powders, suspensions, powders, dusts, pastes, soluble powders, granules, suspension/emulsion concentrates, natural and synthetic materials impregnated with active compound, very fine capsules in polymeric substances and in coating compositions for seed, and furthermore into formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents and/or solid carriers, optionally with the use of surface-active agents, that is, emulsifying agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ammonium salts and ground natural minerals, such as kaolins, clays, talc, chalk, quartz, attapulgite, montmorillonite or diatomaceous earth, and ground synthetic minerals, such highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable; for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from the formulations, as a mixture with other active compounds, such as inesecticides, attractants, sterilizing agents, acaricides, nematicides, fungicides, growth-regulating substances or herbicides.

The insecticides include, for example, phosphates, carbamates, carboxylates, chlorinated hydrocarbons, phenylureas, substances produced by microorganisms and the like.

The following compounds may be mentioned: acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methoxyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos. Demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamdon, phoxim, pirimiphos A, pirimiphos M, propaphos, prothiophos, prothoate, pyraclphos, pyridaphenthion, quinalphos, salithion, sebufos, sulfotep, sulprofos, tetrachlorovinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyri dinyl)-methyl ]-N'-cyano-N-methylethaneimide-amide (NI-25), abamectin, amitrazin, avermectint, azadirachtin, bensultap, bacillus, thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, difenthiuron, diethion, emamectin, fenazaquin, fenbutatin oxide, fenothiocarb, fenpropathrin, fenpyrad, fenpyroximate, fluazinam, fiuazuron, flucyclouron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and also 4-bromo-2-(4-chlorophenyl)-1-(ethoxymethyl)-5-(trifluoromethyl)-1H-pyrrole-3-carbonitrile (AC 303630).

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added itself to be active.

The active compound content of the use forms prepared from the commercially available formulations can very within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The following examples illustrate the present invention more specifically. It should be understood however that the invention is in no way limited to these examples alone.

SYNTHESIS EXAMPLE 1

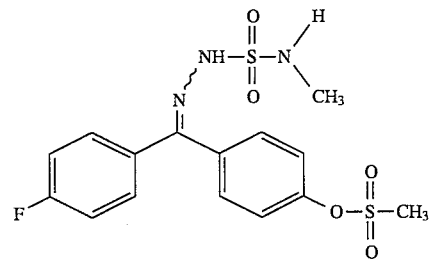

4-Fluoro-4'-methanesulfonyloxybenzophenone hydrazone (3.08 g) and triethylamine (1.20 g) were dissolved in methylene chloride (10 ml), and a solution of N-methylsulfamoyl chloride (1.30 g) in methylene chloride (5 ml) was added dropwise under ice cooling. Subsequently, stirring was carried out at room temperature for 16 hours. After the completion of the reaction, the product was washed with diluted hydrochloric acid and water and dried over anhydrous magnesium sulfate. After the solvent had been distilled off, the product was purified by silica gel column chromatography (n-hexane:ethyl acetate=4:1) to give the desired product N-(4-fluoro-4'-methanesulfonyloxydiphenylmethylimino)-N'-methylsulfamide (2.80 g) as an isomeric mixture (syn-body/anti-body=about 1:1). Melting point: 50°–56° C.

SYNTHESIS EXAMPLE 2

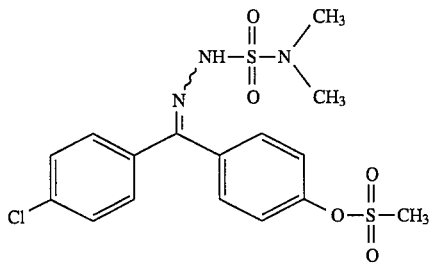

4-Chloro-4'-methanesulfonyloxybenzophenone hydrazone (3.25 g) and 4-N,N-dimethylaminopyridine (1.46 g) were dissolved in toluene (30 ml), and a solution of N,N-dimethylsulfamoyl chloride (1.72 g) in toluene (5 ml) was added dropwise under ice cooling. Subsequently, stirring was carried out for 4 hours under heating and refluxing. After the completion of the reaction, a treatment similar to that in Synthesis Example 1 was carried out to give N-(4-chloro-4'-methanesulfonyloxyphenylmethylminino)-N',N'-dimethylsulfamide (2.2 g) as an isomeric mixture (syn-body/anti-body=about 1:1). Melting point: 55°–60° C.

The following compounds of the formula (I) are obtained in an analogous manner following the general preparation instructions:

TABLE 2

| Compound No. | X | R¹ | R² | R³ | Melting point [°C.] |
|---|---|---|---|---|---|
| 3 | F | CH$_3$ | H | CH$_2$CH$_3$ | 65–70 |
| 4 | Cl | CH$_3$ | H | H | 142–145 |
| 5 | Cl | CH$_3$ | H | CH$_3$ | 67–71 |
| 6 | Cl | CH$_3$ | H | CH$_2$CH$_3$ | 146–147 |
| 7 | Cl | CH$_3$ | H | CH$_2$CH$_2$CH$_3$ | 131–133 |
| 8 | Cl | CH$_3$ | H | CH(CH$_3$)$_2$ | 76–82 |
| 9 | Cl | CH$_3$ | H | CH$_2$CH$_2$CH$_2$CH$_3$ | 120–125 |
| 10 | Cl | CH$_3$ | H | CH$_2$—CO$_2$CH$_3$ | 117–120 |
| 11 | Cl | CH$_3$ | H | CO$_2$—CH$_2$CH$_3$ | 56–61 |
| 12 | Cl | CH$_3$ | H | CO$_2$—C(CH$_3$)$_3$ | 85–89 |
| 13 | Cl | CF$_3$ | H | CH$_2$CH$_3$ | 71–87 |

BIOTEST EXAMPLE

Comparative compound C-1:

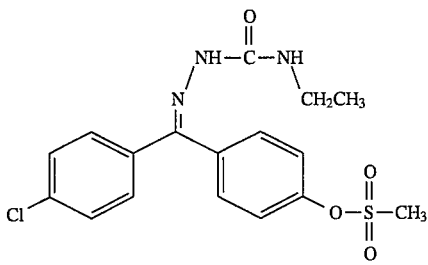

(Compound mentioned in Japanese Patent Laid-Open Application (Kokai) Sho 54-122261)
Test on *Spodoptera litura* larvae
Preparation of test formulations
Solvent: 3 parts by weight xylol
Emulsifier: 1 part by weight polyoxyethylene alkyl phenyl ether To prepare a formulation of an appropriate active compound, 1 part by weight of the active compound was mixed with the above-given amount of the solvent containing the above-given amount of the emulsifier, and the mixture was diluted with water to a given concentration.

Test Method Cabbage leaves were immersed in an aqueous given compound solution having a given concentration and, after the air drying of the solution, they were placed in a petri dish having a diameter of 9 cm. Ten 3rd-instar *Spodoptera litura* larvae were introduced into the petri dish, and the petri dish was placed in a room controlled at a constant temperature of 25° C. After 7 days, the number of dead pests was counted, and the percent mortality was calculated. The test was made in two runs. The results are shown in Table 3.

TABLE 3

| Compound No. | Concentration (ppm) | Percent mortality (%) |
|---|---|---|
| 6 | 40 | 100 |
|   | 8 | 100 |
| 7 | 40 | 100 |
|   | 8 | 100 |
| 8 | 40 | 100 |
|   | 8 | 100 |
| 9 | 40 | 100 |
|   | 8 | 100 |
| 10 | 40 | 100 |
|   | 8 | 100 |
| C-1 | 40 | 100 |
|   | 8 | 0 |

It is understood that the specification and examples are illustrative but not limitative of the present invention and that other embodiments within the spirit and scope of the invention will suggest themselves to those skilled in the art.

We claim:

1. A compound of the formula

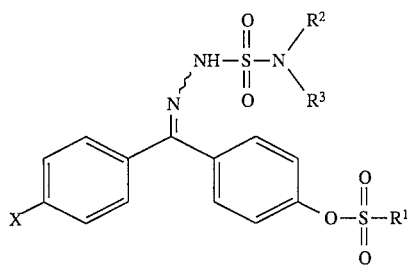

in which

X is halogen or $C_1$–$C_4$-halogenoalkyl, $R^1$ is $C_1$–$C_4$-alkyl or $C_1$–$C_4$-halogenoalkyl, $R^2$ is hydrogen or $C_1$–$C_4$-alkyl, and $R^3$ is hydrogen, $C_1$–$C_4$-alkyl, $C_1$–$C_4$-alkoxycarbonyl or $C_1$–$C_4$-alkoxycarbonylmethyl.

2. A compound according to claim 1, in which

X is fluoro, chloro, bromo or $C_1$–$C_2$-halogenoalkyl, $R^1$ is $C_1$–$C_2$-alkyl or $C_1$–$C_2$-halogenoalkyl, $R^2$ is hydrogen or $CC_1$–$C_2$-alkyl and $R^3$ hydrogen, $C_1$–$C_4$-alkyl, $C_1$–$C_4$-alkoxycarbonyl or $C_1$–$C_2$-alkoxycarbonylmethyl .

3. A compound according to claim 1, in which

X is fluoro, chloro or trifluoromethyl, $R^1$ is methyl or trifluoromethyl, $R^2$ is hydrogen, methyl or ethyl and $R^3$ is hydrogen, methyl, ethyl, n-propyl, i-propyl, n-butyl, methoxycarbonyl, ethoxycarbonyl, tert.-butoxycarbonyl or methoxycarbonyl.

4. A compound according to claim 1, in which

X is fluoro or chloro, $R^1$ is methyl, $R^2$ is hydrogen and $R^3$ is ethyl, n-propyl, isopropyl, butyl or methoxycarbonylmethyl.

5. A compound according to claim 1, wherein such compound is N-(4-chloro-4'-methanesulfonyloxydiphenylimino)-N'-ethylsulfamide of the formula

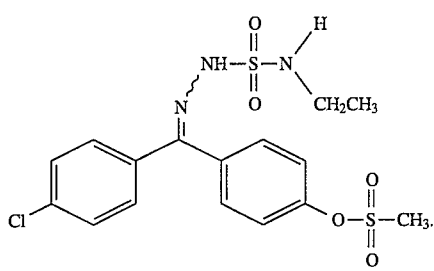

6. A compound according to claim 1, wherein such compound is N-(4-chloro-4'-methanesulfonyloxydiphenylimino)-N'-propylsulfamide of the formula

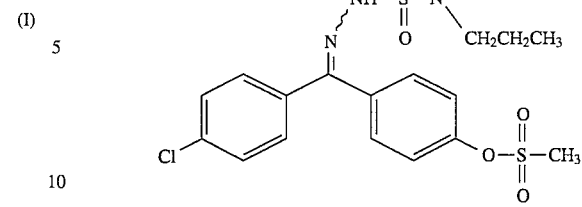

7. A compound according to claim 1, wherein such compound is N-(4-chloro-4'-methanesulfonyloxydiphenylimino)-N'-isopropylsulfamide of the formula

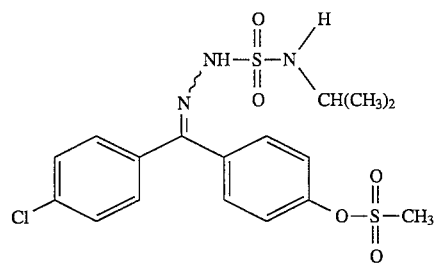

8. A compound according to claim 1, wherein such compound is N-(4-chloro-4'-methanesulfonyloxydiphenylimino)-N'-butylsulfamide of the formula

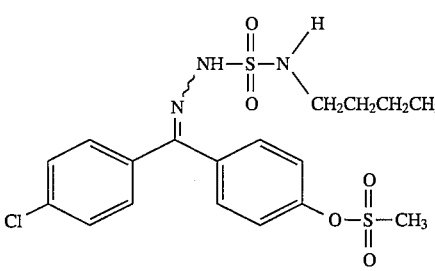

9. A compound according to claim 1, wherein such compound is N-(4-chloro-4'-methanesulfonyloxydiphenylimino)-N'-methoxycarbonylmethylsulfamide of the formula

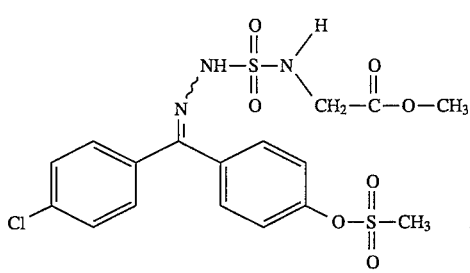

10. A composition for combating animal pests which comprises an animal-pest pesticidally effective amount of a compound according to claim 1 and a diluent.

11. A method of combating animal pests which comprises applying to animals or an animal habitat an animal-pest pesticidally effective amount of a compound according to claim 1.

12. The method according to claim 11, wherein said compound is

N-(4-chloro-4'-methanesulfonyloxydiphenylimino)-N'-ethylsulfamide,
N-(4-chloro-4'-methanesulfonyloxydiphenylimino)-N'-propylsulfamide,
N-(4-chloro-4'-methanesulfonyloxydiphenylimino)-N'-isopropylsulfamide,
N-(4-chloro-4'-methanesulfonyloxydiphenylimino)-N'-butylsulfamide, or
N-(4-chloro-4'-methanesulfonyloxydiphenylimino)-N'-methoxycarbonylmethylsulfamide.

* * * * *

UNITED STATES PATENT AND TRADEMARK OFFICE
CERTIFICATE OF CORRECTION

PATENT NO. : 5,596,017
DATED : January 21, 1997
INVENTOR(S) : Otsu, et al.

It is certified that error appears in the above-indentified patent and that said Letters Patent is hereby corrected as shown below:

Col. 11, line 37   Delete " methoxycarbonyl " and substitute -- methoxycarbonylmethyl --

Signed and Sealed this

Twenty-second Day of July, 1997

Attest:

BRUCE LEHMAN

Attesting Officer

Commissioner of Patents and Trademarks